(12) United States Patent
Charvet et al.

(10) Patent No.: US 12,023,064 B2
(45) Date of Patent: Jul. 2, 2024

(54) ROTARY INSTRUMENTS AND METHODS FOR INTRAUTERINE TISSUE RESECTION

(71) Applicant: Caldera Medical, Inc., Agoura Hills, CA (US)

(72) Inventors: Jose Luis Charvet, Agoura Hills, CA (US); Felix Lu, Agoura Hills, CA (US); Sandra Muhlfeld, Thousand Oaks, CA (US)

(73) Assignee: Caldera Medical, Inc., Westlake Village, CA (US)

( * ) Notice: Subject to any disclaimer, the term of this patent is extended or adjusted under 35 U.S.C. 154(b) by 1218 days.

(21) Appl. No.: 16/185,502

(22) Filed: Nov. 9, 2018

(65) Prior Publication Data

US 2019/0133640 A1    May 9, 2019

Related U.S. Application Data

(60) Provisional application No. 62/626,431, filed on Feb. 5, 2018, provisional application No. 62/584,059, filed on Nov. 9, 2017.

(51) Int. Cl.
| | | |
|---|---|---|
| *A61B 17/32* | (2006.01) | |
| *A61B 1/00* | (2006.01) | |
| *A61B 1/015* | (2006.01) | |
| *A61B 1/018* | (2006.01) | |

(Continued)

(52) U.S. Cl.
CPC .... *A61B 17/32002* (2013.01); *A61B 1/00071* (2013.01); *A61B 1/00103* (2013.01); *A61B 1/00163* (2013.01); *A61B 1/00195* (2013.01); *A61B 1/015* (2013.01); *A61B 1/018* (2013.01); *A61B 17/42* (2013.01); *A61B 2017/0023* (2013.01); *A61B 2017/00398* (2013.01); *A61B 2017/00734* (2013.01); *A61B 2017/320024* (2013.01); *A61B 2017/4216* (2013.01); *A61B 2217/005* (2013.01); *A61B 2217/007* (2013.01)

(58) Field of Classification Search
CPC . A61B 17/42; A61B 1/00071; A61B 1/00103; A61B 1/00163; A61B 1/00195; A61B 1/015; A61B 1/018; A61B 17/32002; A61B 2017/0023; A61B 2017/00398; A61B 2017/00734; A61B 2017/320024; A61B 2017/4216; A61B 2217/005; A61B 2217/007
USPC ....... 227/175.1; 600/105, 130, 84, 170, 180; 604/22; 606/84, 170, 180, 22
See application file for complete search history.

(56) References Cited

U.S. PATENT DOCUMENTS

| | | | |
|---|---|---|---|
| 4,108,182 A | | 8/1978 | Hartman et al. |
| 4,292,961 A | * | 10/1981 | Kawashima ............. A61B 1/31 |
| | | | 600/117 |
| 4,646,738 A | | 3/1987 | Trott |

(Continued)

FOREIGN PATENT DOCUMENTS

CA        2132286 C      8/2004

OTHER PUBLICATIONS

WIPO, U.S. International Search Authority, International Search Report and Written Opinion dated Jan. 16, 2019 in International Patent Application No. PCT/US2018/060013, 10 pages.

*Primary Examiner* — Timothy J Neal
(74) *Attorney, Agent, or Firm* — Inskeep IP Group, Inc.

(57) ABSTRACT

A compact multi-lumened hysteroscope, a single-use tissue resector, and a medical system employing the same for diagnosis and therapeutic treatment of uterine tissue, such as polyps and fibroids.

16 Claims, 10 Drawing Sheets

(51) Int. Cl.
*A61B 17/42* (2006.01)
*A61B 17/00* (2006.01)

(56) References Cited

U.S. PATENT DOCUMENTS

| | | | |
|---|---|---|---|
| 4,815,462 A | | 3/1989 | Clark |
| 5,286,253 A | | 2/1994 | Fucci |
| 5,290,303 A | * | 3/1994 | Pingleton ......... A61B 17/32002 606/170 |
| 5,665,101 A | * | 9/1997 | Becker ................. A61M 1/842 606/167 |
| 6,068,641 A | * | 5/2000 | Varsseveld ....... A61B 17/32002 606/170 |
| 8,702,702 B1 | * | 4/2014 | Edwards .......... A61B 17/32002 606/50 |
| 10,448,811 B2 | * | 10/2019 | London Brown ....... A61B 1/05 |
| 2003/0114873 A1 | * | 6/2003 | Banko ................ A61F 9/00745 606/169 |
| 2004/0092992 A1 | * | 5/2004 | Adams ............. A61B 17/32002 606/180 |
| 2005/0096649 A1 | * | 5/2005 | Adams ................. A61B 18/149 606/171 |
| 2005/0288551 A1 | * | 12/2005 | Callister ................ A61F 6/225 600/114 |
| 2007/0068990 A1 | * | 3/2007 | Shelton ............ A61B 17/07207 227/175.1 |
| 2007/0129605 A1 | | 6/2007 | Schaaf |
| 2011/0118544 A1 | * | 5/2011 | Adams .................. A61B 1/015 600/156 |
| 2012/0209074 A1 | | 8/2012 | Titus |
| 2013/0165857 A1 | * | 6/2013 | O'Donnell ........ A61M 39/0606 604/95.04 |
| 2013/0184520 A1 | * | 7/2013 | Lee ........................ A61B 17/02 600/37 |
| 2013/0184691 A1 | * | 7/2013 | Oskin ................ A61B 1/00128 606/1 |
| 2014/0031834 A1 | * | 1/2014 | Germain ................ A61B 1/018 606/119 |
| 2014/0142393 A1 | | 5/2014 | Piskun et al. |
| 2014/0324065 A1 | * | 10/2014 | Bek ........................ A61B 50/13 606/110 |
| 2017/0056102 A1 | * | 3/2017 | Germain ............ A61B 18/1485 |
| 2019/0223898 A1 | * | 7/2019 | Curtin .............. A61B 17/32002 |

* cited by examiner

ROTARY INSTRUMENTS AND METHODS FOR INTRAUTERINE TISSUE RESECTION

RELATED APPLICATIONS

This application claims priority to U.S. Provisional Application Ser. No. 62/584,059 filed Nov. 9, 2017, entitled Rotary Instruments and Methods for Intrauterine Tissue Resection and U.S. Provisional Application Ser. No. 62/626,431 filed Feb. 5, 2018, entitled Rotary Instruments and Methods for Intrauterine Tissue Resection, both of which are hereby incorporated herein by reference in their entireties.

FIELD OF THE INVENTION

The present invention relates to the field of uterine tissue diagnosis and therapeutic treatments such as resection and, more particularly, to instruments for the rotary removal of uterine tissue and methods of use thereof.

BACKGROUND OF THE INVENTION

Hysteroscopy broadly refers to the inspection of a uterine cavity using a hysteroscope accessed through the cervix. Hysteroscopy allows for diagnosis of intrauterine pathology and, furthermore, can be used for surgical intervention. The hysteroscope typically includes a sheath, scope and various channels for fluid control, and a working channel for insertion of therapeutic instruments, such as tissue removal devices.

One problem associated with current hysteroscopy systems is that they are intended for use in an operating room setting with the patient being subjected to some type of anesthesia. Anesthesia is required in particular because the size of current hysteroscopes is relatively large and, as such, they can cause discomfort and pain to the patient. For example, typical hysteroscopes have an outermost diameter of at least 6.2 millimeters and often larger.

Another problem with current systems is that the resector or tissue removal devices are relatively large, complex and, hence, relatively expensive pieces of equipment. Accordingly, current resectors are multi-use components requiring special handling, cleaning, and sterilization procedures. Currently marketed tissue removal systems have large outflow cross-sectional areas, requiring the hysteroscopes to have large inflow channels (and thereby larger diameter hysteroscopes) to maintain fluid balance inside the uterus. When using a hanging bag which is typically used in office procedures (as opposed to fluid management systems used in hospitals) a large outflow equates to less cutting time for the tissue removal device because water exits the uterus faster thereby losing the distension needed to allow cutting faster.

What is needed in the field, therefore, is a compact hysteroscope that avoids the need for use of anesthesia, has better control of fluid balance when, for example, using a hanging bag fluid source and, hence, can be used in an office setting and a simplified, efficient single-use resector that does not require special handling, cleaning, and sterilization procedures, and medical systems employing the same.

OBJECTS AND SUMMARY OF THE INVENTION

The present invention provides a compact hysteroscope that avoids the need for use of anesthesia, have better control of fluid balance when using a hanging bag fluid source and, hence, that can be used in an office setting and simplified, efficient single-use resector that does not require special handling, cleaning, and sterilization procedures, and medical systems employing the same. These objectives are achieved, in part, by providing a single-use uterine tissue resector comprising: a handle; an elongated outer cutting tube having a proximal portion statically attached to the handle; an elongated inner cutting tube concentrically positioned and rotatable within a lumen of the outer cutting tube; and a motor positioned within the handle and coupled to a proximal end of the inner cutting tube, wherein upon activation of the motor, the motor rotates the inner cutting tube relative to the outer cutting tube. Wherein the single-use uterine tissue resector further comprises a battery positioned within the handle that is in electrical communication with the motor; wherein the handle comprises a leaf spring trigger; wherein the handle comprises a momentary switch; wherein a distal end of the inner cutting tube and a distal end of the outer cutting tube form openings into a lumen of the inner cutting tube; wherein a distal portion of the inner cutting tube and a distal portion of the outer cutting tube comprise apertures having cutting surfaces; wherein the apertures of the inner and outer cutting tubes comprise a substantially same size, shape and longitudinal placement relative to one another; wherein the single-use uterine tissue resector further comprises a fluid chamber positioned within the handle having a lateral port that protrudes out from the handle; wherein a proximal portion of the inner cutting tube passes through the fluid chamber, the proximal portion of the inner cutting tube having an aperture formed through a sidewall thereof; and wherein the handle comprises a window through which the lateral port of the fluid chamber protrudes and is rotatable relative to the handle.

These objectives are further achieved, in part, by providing a hysteroscope comprising: a proximal body from which a multi-lumened elongated distal outer tube extends; an optical lumen positioned through the proximal body and the distal outer tube having a fluid-sealed distal end and a proximal optical output; a light transmission lumen positioned through the proximal body and the distal outer tube having a fluid-sealed distal end and a proximal light post configured for attachment to a light source; a working lumen positioned through the proximal body and the distal outer tube having an open distal end and an open proximal end and configured to receive a medical instrument inserted therethrough; and a first irrigation lumen positioned through the proximal body and the distal outer tube having an open distal end and a proximal valve. Wherein the proximal body comprises a feature that allows attachment of a handle or attachment to an examination table; wherein the optical lumen, the working lumen and the irrigation lumen are positioned within the light transmission lumen; and wherein the hysteroscope further comprises a second irrigation lumen positioned through the proximal body and the distal outer tube having an open distal end and a proximal valve.

These objectives are further achieved, in part, by providing a medical system comprising: a single-use uterine tissue resector comprising: a handle; an elongated outer cutting tube having a proximal portion statically attached to the handle; an elongated inner cutting tube concentrically positioned and rotatable within a lumen of the outer cutting tube; and a motor positioned within the handle and coupled to a proximal end of the inner cutting tube, wherein upon activation of the motor, the motor rotates the inner cutting tube relative to the outer cutting tube; and a hysteroscope comprising: a proximal body from which a multi-lumened elongated distal outer tube extends; an optical lumen positioned through the proximal body and the distal outer tube having a fluid-sealed distal end and a proximal optical output; a light transmission lumen positioned through the proximal body and the distal outer tube having a fluid-sealed distal end and a proximal light post configured for attachment to a light source; a working lumen positioned through the proximal body and the distal outer tube having an open distal end and an open proximal end and through which the resector is reversibly inserted; and a first irrigation lumen positioned through the proximal body and the distal outer tube having an open distal end and a proximal valve. Wherein the medical system further comprises a modular flow channel reversibly insertable through the working channel of the hysteroscope; wherein the optical lumen, the working lumen and the irrigation lumen are positioned within the light transmission lumen of the hysteroscope; wherein the distal outer tube of the hysteroscope comprises an outer diameter of about 5.8 millimeters; wherein the resector further comprises a battery positioned within the handle that is in electrical communication with the motor; and wherein the handle comprises a leaf spring trigger and a momentary switch.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
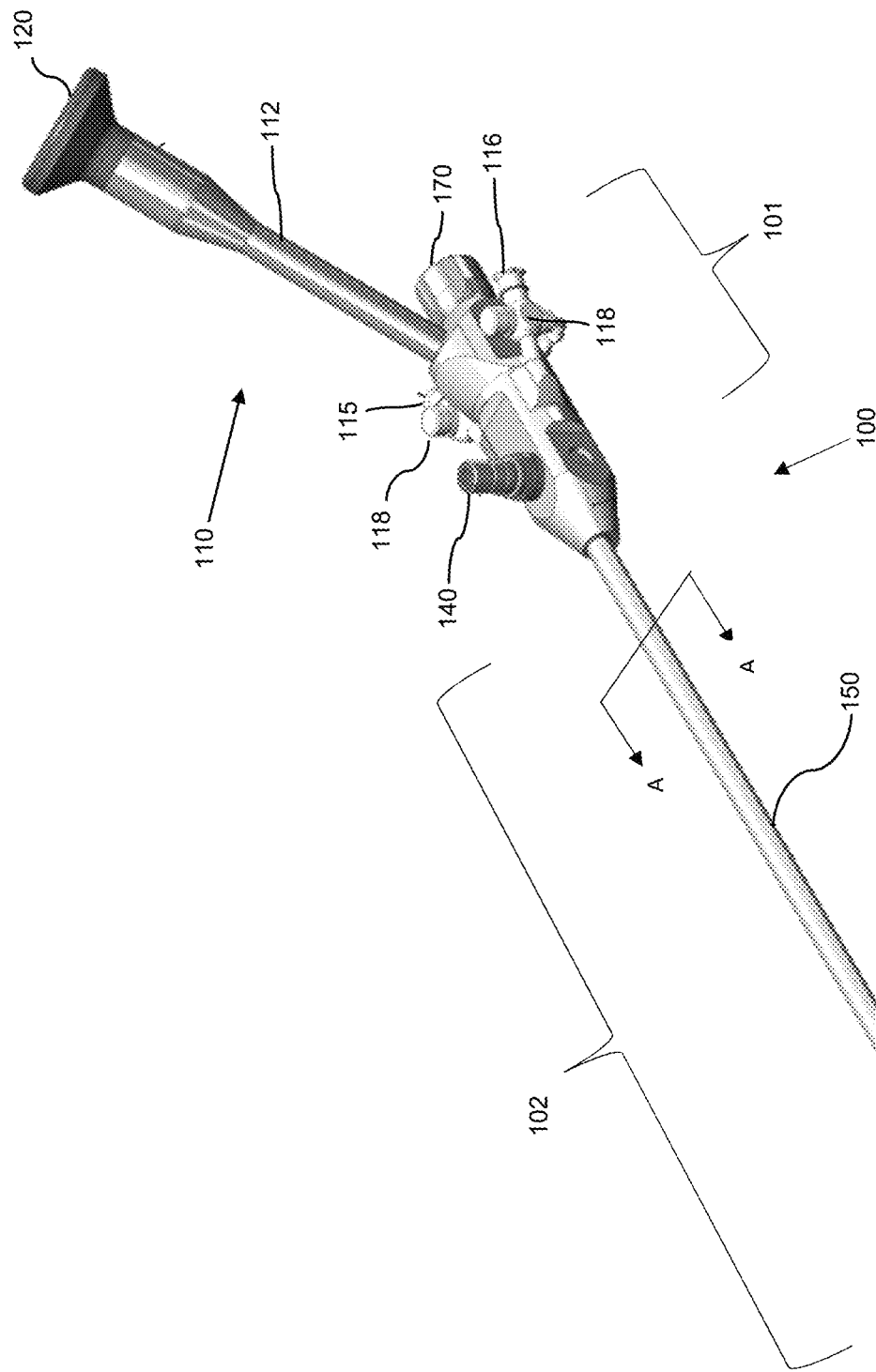
FIG. 1 is a perspective view of one embodiment of a hysteroscope according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present invention is directed to a system comprising a reusable or multi-use, multi-lumen hysteroscope for uterine distention and visualization of uterine tissue and/or tissue pathology and a single-use tissue removal device (TRD) or tissue resector to mechanically remove pathological tissues and irrigate such from the uterus.

Herein, detailed elements of a hysteroscope according to the present invention are disclosed. Generally speaking, in one embodiment of the present invention, the hysteroscope is a multi-lumen, for example a five-lumen, apparatus having an optical system to enable viewing of the pathology; a connector for a light source to illuminate the area of interest inside the uterus; a working channel for accepting a tissue resector or other instrument and for facilitating fluid out flow, e.g. via a vacuum; and two independent irrigation or inflow channels associated with valves, e.g. mechanical valves, that work in conjunction with the central channel out flow element to distend the uterus during diagnostic (pathology identification) and therapeutic (pathology removal) procedures.

In certain embodiments, the hysteroscope functions both as a diagnostic (pathology identification) and therapeutic (pathology removal) tool. In one embodiment for the diagnostic procedure, the hysteroscope is configured to seal the working channel from fluid transport and employ one irrigation channel for fluid inflow and another irrigation channel for fluid outflow, e.g. via a vacuum source. This configuration may negate the need for employing a modular outflow channel (described below). If a tissue pathology is identified during the diagnostic procedure, the configuration of the hysteroscope can be converted to the previously described configuration and a resector is inserted into the working channel for removal of the relevant tissue. When switching to the therapeutic portion, both inflow and outflow tubes are removed from the irrigation channels and replaced with a custom Y-tubing providing fluid inflow.

Figure 2:
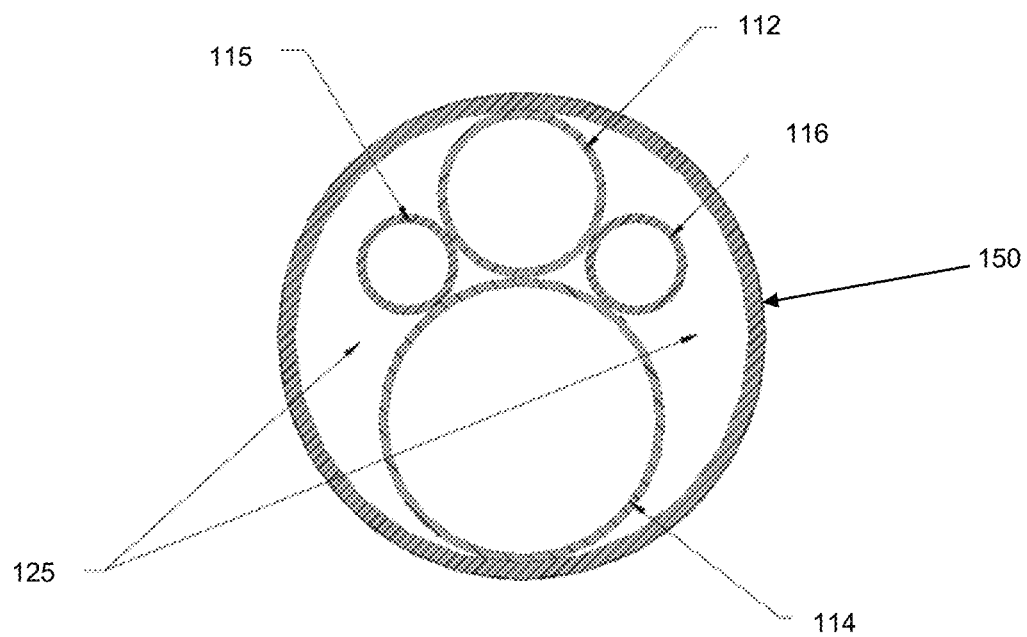
FIG. 2 is cross-sectional view of one embodiment of a hysteroscope according to the present invention, taken along the line A-A shown in FIG. 1.
Figure 3:
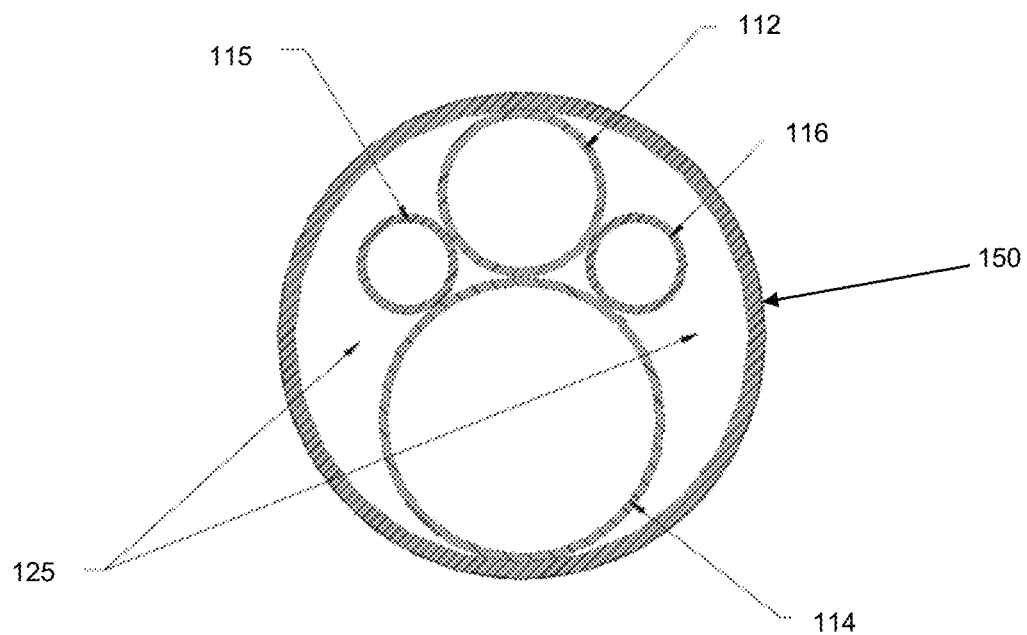
FIG. 3 is a view of a distal end of one embodiment of a hysteroscope according to the present invention.

With reference to FIGS. 1-3, a hysteroscope 100 is comprised of an operation section or body 101 at the proximal portion and an elongated tube as an insertion section 102 at the distal portion. The operation section or the body 101 at the proximal end further comprises an optical system 110 employing an optical or first lumen 112. The proximal end 120 of the first lumen 112 protrudes upwardly from the body 101 towards a viewer and is provided with an optical output or eyepiece at the terminal end for user observation. Alternatively, the proximal portion of the first lumen 112 employs an optical cable coupling element for connection and image viewing on a remote screen. A distal portion of the first lumen 112 is located inside the insertion section 102. The optical system enables optimal viewing of the pathology by, for example, housing a train of rod lenses and spacers inside the first lumen 112. A distal end of the lumen 112 is sealed to prevent entry of fluid in to the lumen 112.

A second lumen 114 is located at the proximal portion of the body 101 underneath the first lumen 112 and extends into insertion section 102 at the distal portion (FIGS. 2 and 3). The second lumen 114 functions as a working channel, for example, for receiving an instrument such as a single-use tissue removal device (TRD) or tissue resector 300 and has an opening at a distal and proximal end and a seal 170 at a proximal portion to allow fluid sealing and/or a friction fit with the inserted instrument, e.g. a tissue resector and/or a modular outflow channel.

The proximal portion of the body 101 of the hysteroscope 100 further comprises a third irrigation lumen 115 and a fourth irrigation lumen 116, wherein both lumens extend through and to a distal end of the insertion section 102 of the hysteroscope 100. The third and fourth lumens are located laterally and symmetrically between the first lumen 112 and the second lumen 114. The third and fourth lumens are independent irrigation lumens or channels having openings at the distal end of the body 101, (FIGS. 2 and 3) and valves 118 at their proximal portions to control the flow of fluid therethrough in order to keep the uterus distended and pressure maintained with a fluid medium during diagnostic and therapeutic procedures.

The insertion section 102 of the hysteroscope comprises a single tubing or barrel 150 enclosing the distal portions and ends of the first lumen 112 of the optical system, the second lumen 114 of the working channel, and the third lumen 115 and fourth lumen 116 of the irrigation channels (FIGS. 2 and 3).

Cross-sectional and distal end views of the single tubing or barrel 150 of the insertion section 102 of the hysteroscope 100, FIGS. 2 and 3, show the arrangement of the distal portions of the first lumen 112, second lumen 114, third lumen 115 and fourth lumen 116 inside the lumen of the barrel 150. FIG. 2 shows a cross-sectional view of a mid-portion of the barrel 150 shown in FIG. 1. As can be seen in FIG. 2, the wall of the single tubing or barrel 150 encloses all the distal portions of the first lumen 112, second lumen 114, third lumen 115 and fourth lumen 116. The first lumen 112 is located superiorly inside the barrel for the optical system to enable viewing of the pathology and is sealed to fluid at the distal end. The second lumen 114 or working channel is located inferior to the first lumen 112. The third lumen 115 and the fourth lumen 116 for irrigation are located laterally and symmetrically between the first lumen 112 and the second lumen 116.

A space 125 created by the inner wall of the barrel 150 and the outer walls of all four lumens is completely or partially occupied by a light transmission element or elements, e.g. by fiber optic cables or bundles connected to the light post 140 (FIG. 1) proximally positioned on the body 101 of the hysteroscope 100. At the distal end of the barrel 150, the space 125 is sealed from fluid entry, e.g. by a clear or transparent adhesive, so that light can be transmitted from the light post 140 out the distal end of the barrel 150 and into the uterus.

FIG. 3 shows a distal end view of the multi-lumen tubing or barrel 150. As can be seen in FIG. 3, barrel 150 encloses all four distal ends of the first lumen 112, second lumen 114, third lumen 115 and fourth lumen 116 in a configuration similar to that described with regard to FIG. 2.

It will be understood that while the various lumens employed within the lumen of the barrel 150 have been described and shown in a particular configuration relative to one another, the various lumens may be arranged in alternative orientations and still be within the scope of the present invention. It will also be understood that while the various lumens are shown as having circular cross-sectional shapes, the lumens may employ any regular or irregular cross-sectional shapes. The cross-sectional shapes of the various lumens may be the same relative to one another or may vary relative to one another.

According to some embodiments, a diameter of the barrel 150 of the multi-lumen instrument is uniform along a longitudinal length or is variable along a longitudinal length. In some embodiments, the barrel 150 outer diameter, OD, is 5.8 mm, which is unique and advantageous in that it is smaller than standard hysteroscopes having an OD of 6.2 mm. According to some embodiments, the cross-sectional shape of the barrel 150 of the multi-lumen instrument is uniform along a longitudinal length or is variable along a longitudinal length. The cross-sectional shape the barrel 150 of the multi-lumen instrument may be circular, as shown, or may be any other regular or irregular shape.

In some embodiments, the proximal portion of the body 101 of the hysteroscope 100 employs exterior features to allow attachment of a handle or a hospital table clamp to the hysteroscope 100.

Figure 11:
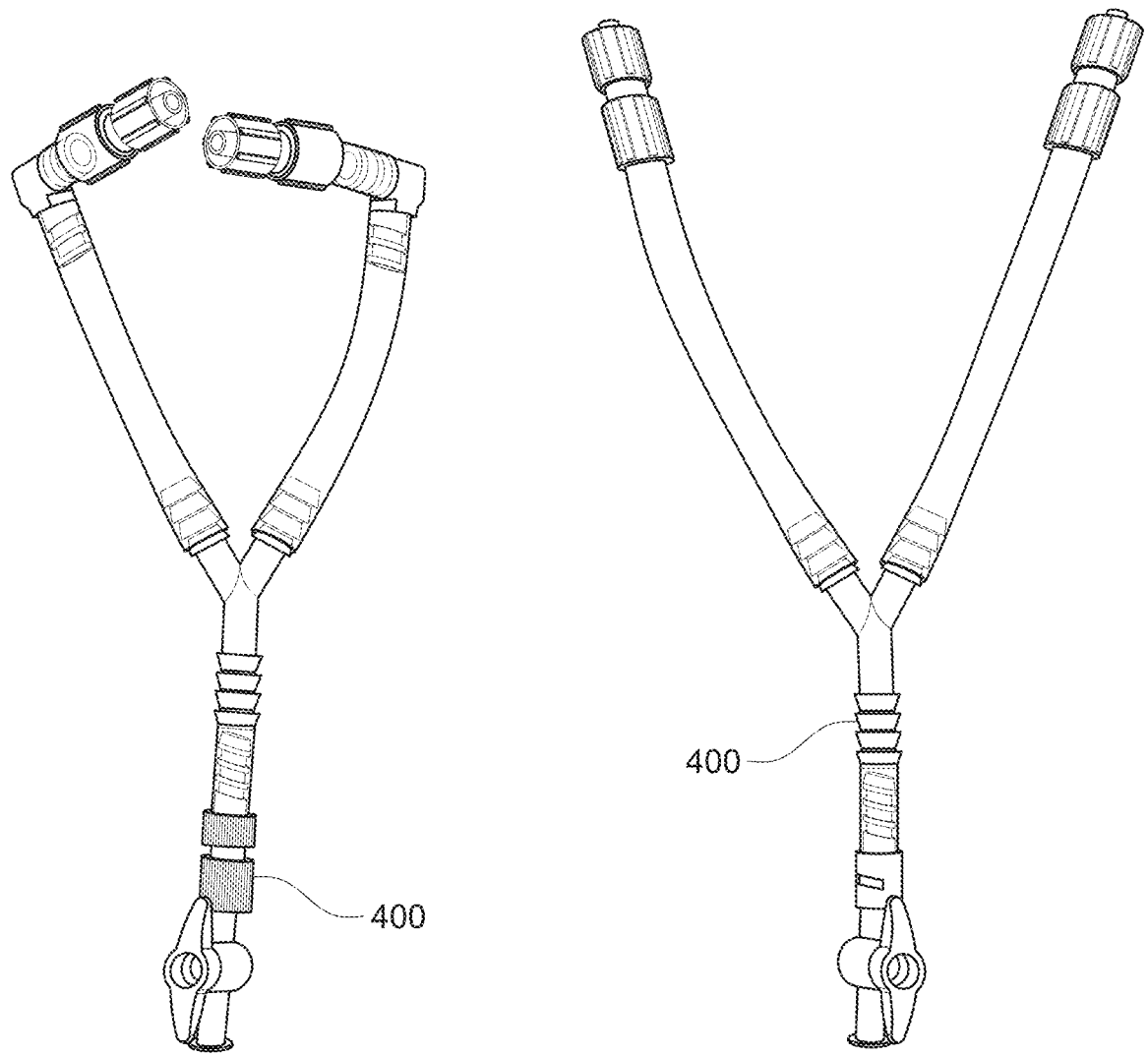
FIG. 11 is a perspective view of certain embodiments of a Y-tubing of a hysteroscope according to the present invention.

FIG. 11, shows various configurations of a Y-tubing 400 having distal ends employed in certain embodiments to attach to the proximal portions of the third and fourth irrigation lumens 115 and 116 and a proximal end for attachment to a fluid inflow source.

Figure 4:
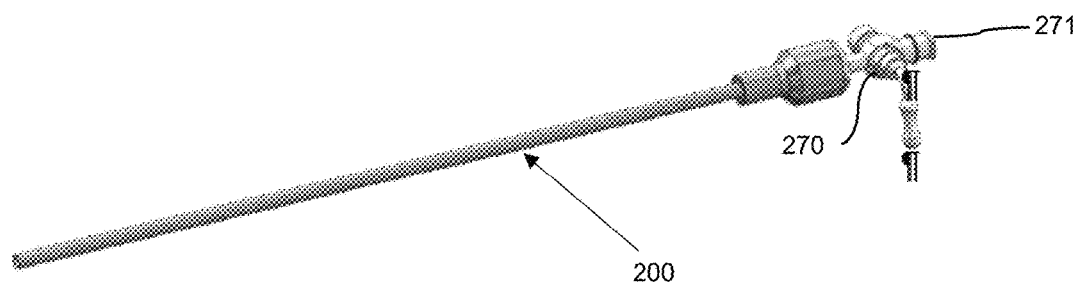
FIG. 4 is a perspective view of one embodiment of a modular outflow channel according to the present invention.
Figure 5A:
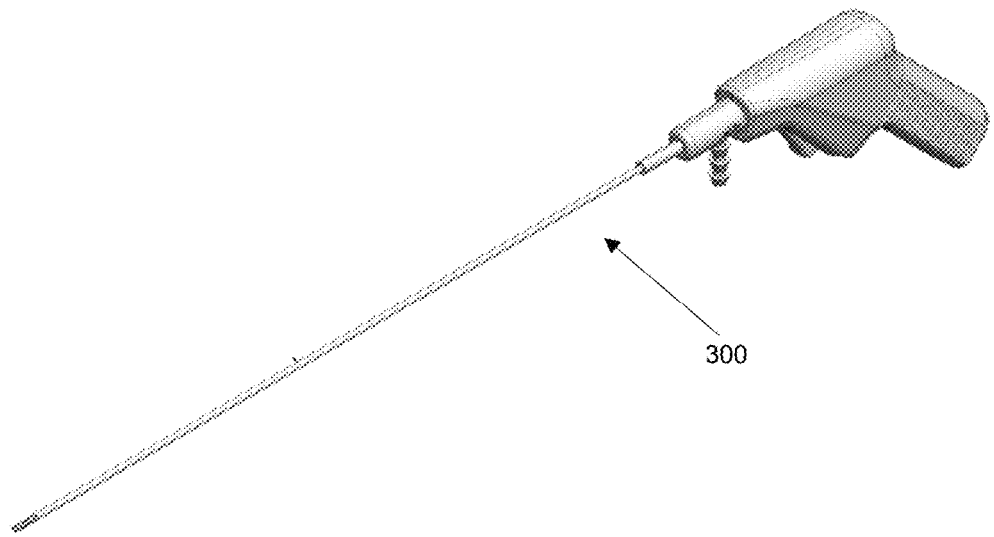
FIG. 5A is a perspective view of one embodiment of a tissue resector according to the present invention.
Figure 5B:
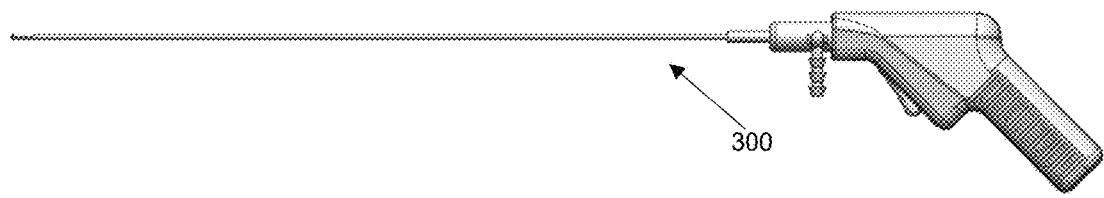
FIG. 5B is a side view of one embodiment of a tissue resector according to the present invention.
Figure 5C:
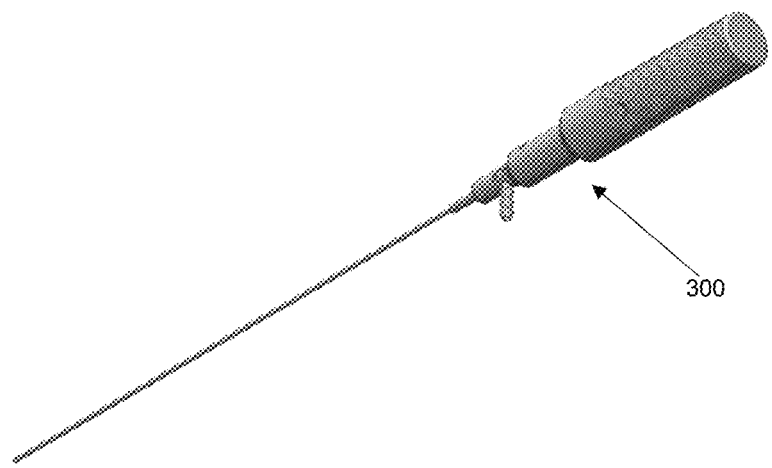
FIG. 5C is a perspective view of one embodiment of a tissue resector according to the present invention.
Figure 5D:
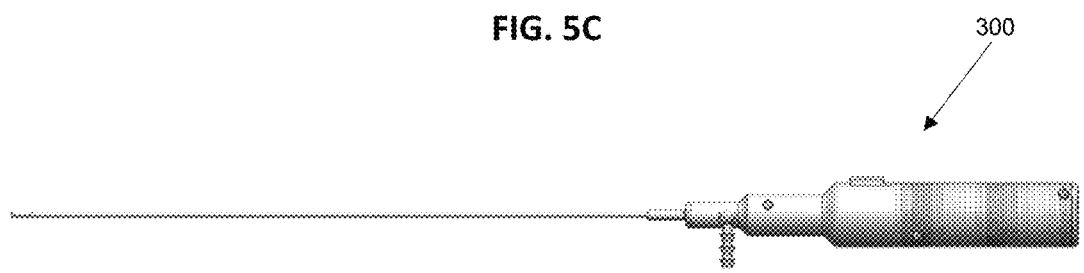
FIG. 5D is a top view of one embodiment of a tissue resector according to the present invention.

In certain embodiments of the present invention, as shown in FIG. 4, the system of the present invention includes a modular outflow channel 200 sized for insertion through the working channel 114 of the hysteroscope 100. A lumen is formed through an interior of the channel 200 having a distal and proximal end that are open. A proximal portion of the modular outflow channel 200 comprises an outflow port 271 and a valve 270 that function to regulate fluid outflow and pressure to distend the uterus. This instrument can be optionally used during the diagnostic procedure to view the pathologies and uterine cavity. After the diagnostic procedure, the outflow channel is removed and the TRD is inserted.

Hereafter, a single-use, tissue removal device (TRD) or tissue resector is described according to the present invention. With reference to FIGS. 5A-10B, the inventive tissue resector is a dual-lumen, tissue cutting instrument capable of removing and irrigating cut tissue from, for example, a uterus. The resector is a single-use tool disposable after initial use, and comprises a handle, an inner cutting tube and an outer cutting tube, where the inner cutting tube is rotated by a motor housed inside the handle and the outer cutting tube is rigidly bonded or otherwise attached to the handle. In some embodiments, the uterine tissue resector is battery operated. The entire resector is single-use, meaning it can be provided clean, sterile and be disposed of after use. This also means it is designed to be cost effective and have a shelf life.

Figure 6A:
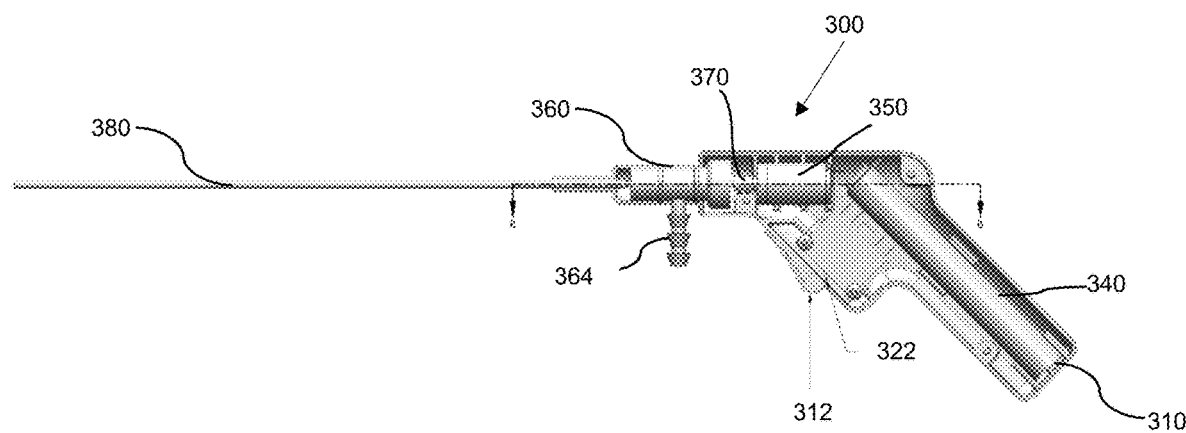
FIG. 6A is a side cross-sectional view of one embodiment of a tissue resector according to the present invention.
Figure 6B:
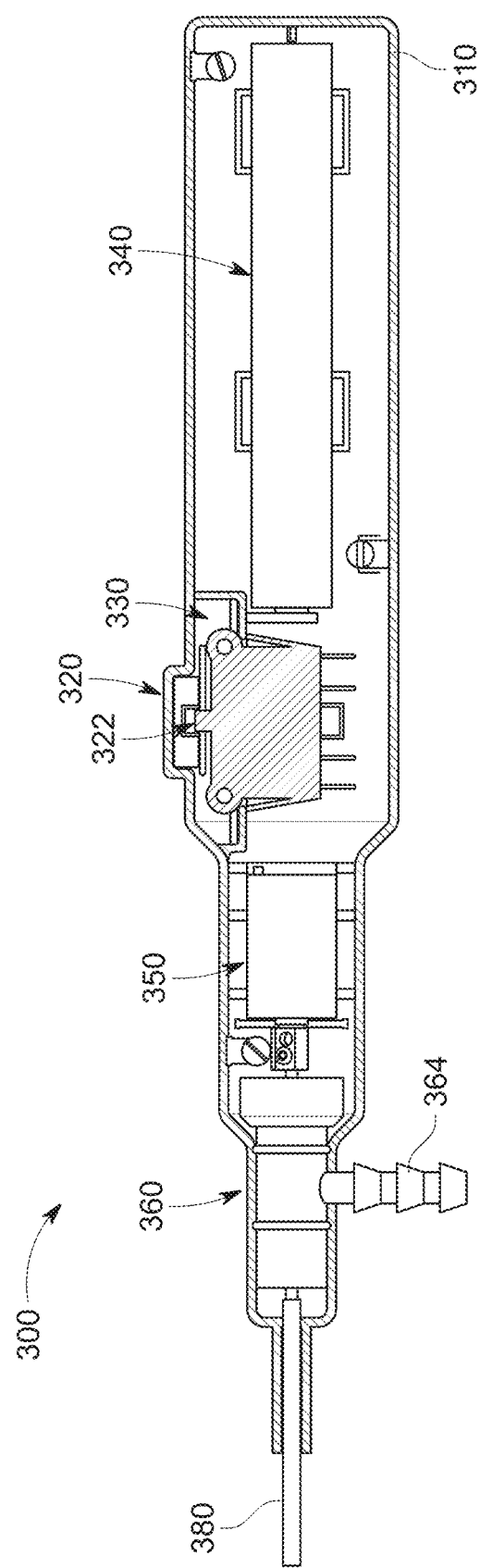
FIG. 6B is a top cross-sectional view of one embodiment of a tissue resector according to the present invention.
Figure 6C:
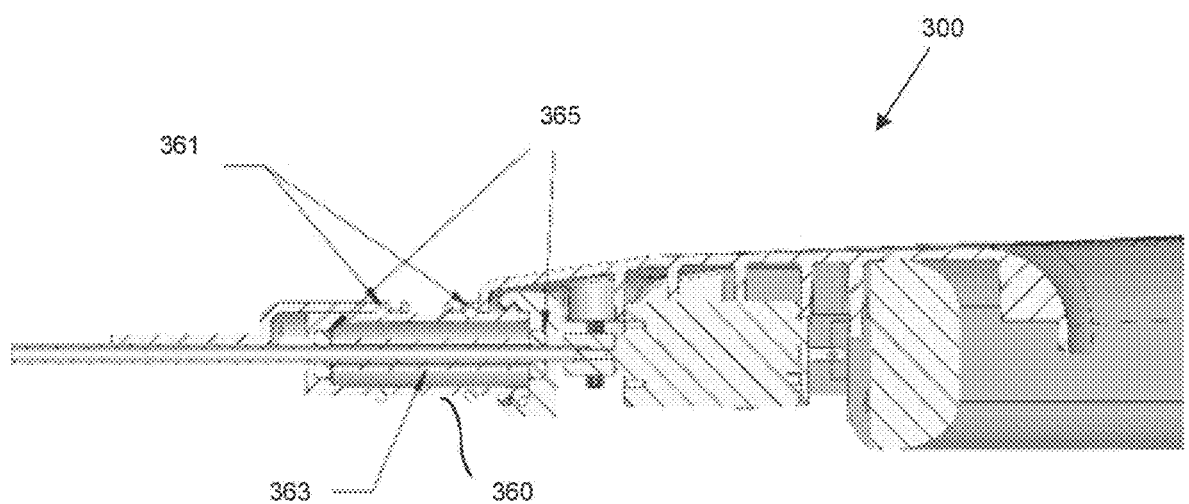
FIG. 6C is a partial, bottom cross-sectional view of one embodiment of a tissue resector according to the present invention, taken along line B-B shown in FIG. 6A.

FIGS. 5A-5D show exemplary embodiments of the single-use tissue removal device (TRD) or tissue resector 300. FIGS. 6A-6C show cross-sectional and/or semi-transparent views of the tissue resector 300. As seen in FIGS. 6A and 6B, the tissue resector 300 comprises a handle 310 with an integrated leaf spring trigger 312; a momentary switch 320 with a switch button 322 contained in a sealed chamber 330; an internal battery or battery pack 340; a motor 350; an irrigation chamber 360; a coupler 364 and a dual lumen cutting tube assembly 380.

Figure 7:
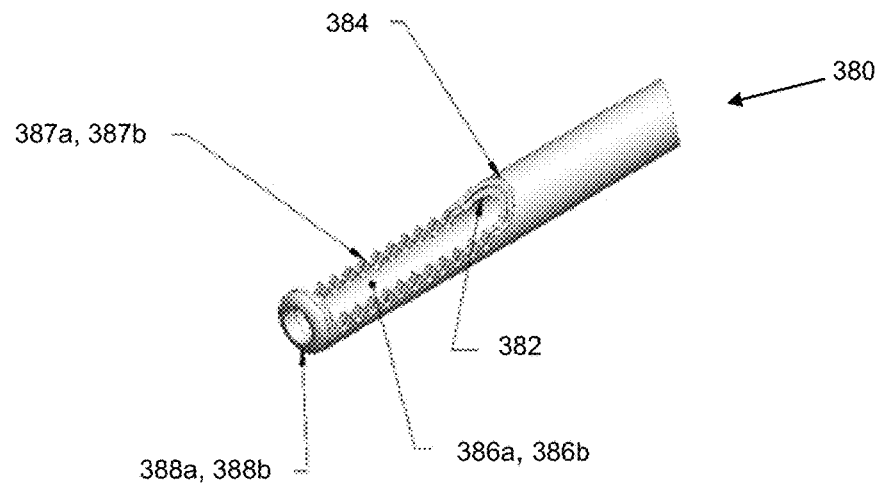
FIG. 7 is a perspective view of a distal portion of one embodiment of a tissue resector according to the present invention.

An enlarged view of the dual lumen cutting tube assembly 380 of the uterine tissue resector 300 is shown in FIG. 7. The cutting tube assembly 380 comprises an inner cutting tube 382 with a cutting aperture or window 386a in the distal portion and an outer cutting tube 384 with a cutting aperture or window 386b in the distal portion that align with one another. Both a periphery of the aperture or window 386a of the inner cutting tube 382 and a periphery of the aperture or window 386b of the outer cutting tube 384 have sharp cutting surfaces, e.g. cutting projections or teeth, 387a and 387b, geometrically formed by a series of scallops along the cutting edge to cut the pathological tissue into pieces small enough to be irrigated through an inner lumen of inner cutting tube 382 and to the irrigation chamber 360.

As shown in FIG. 7, both the distal ends of the inner cutting tube 382 and outer cutting tube 384 employ distal holes 388a, 388b. The distal holes 388a, 388b allow fluid irrigation, e.g. via suction, during instances when rotation of inner cutting tube 384 results in the closure of cutting window 386b of outer cutting tube 384.

Figure 10A:
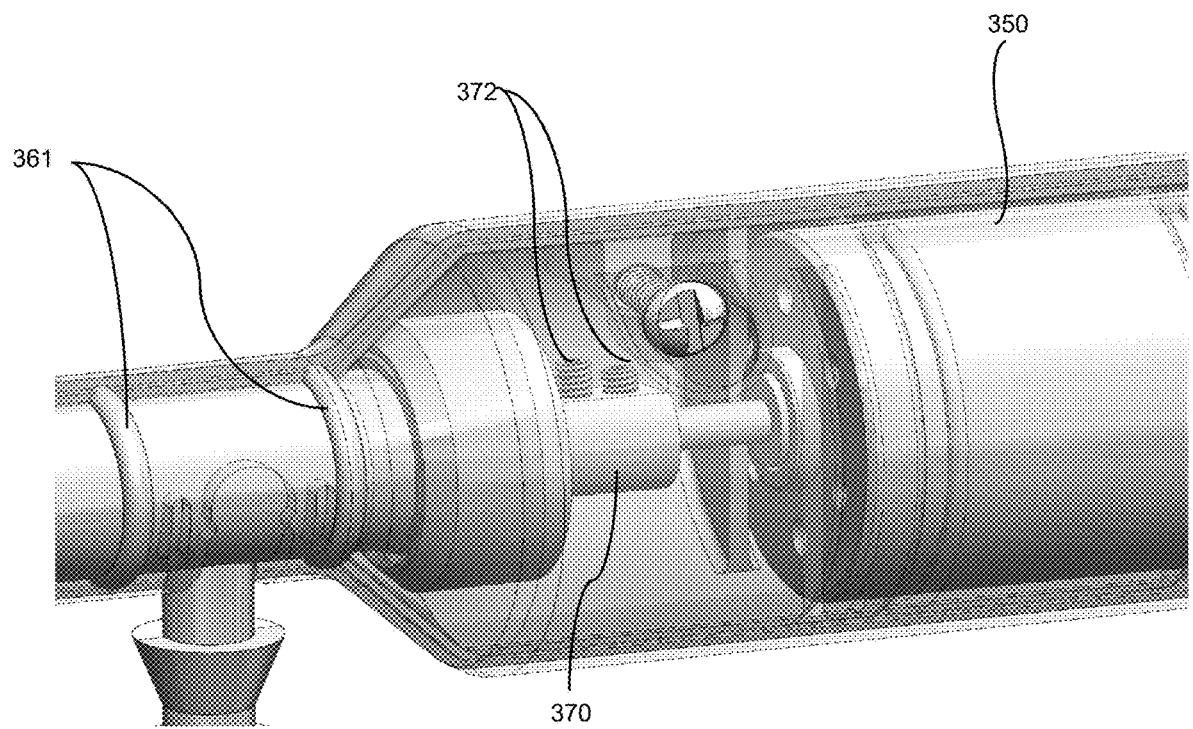
FIG. 10A is a partial transparent perspective view of one embodiment of a tissue resector according to the present invention.
Figure 10B:
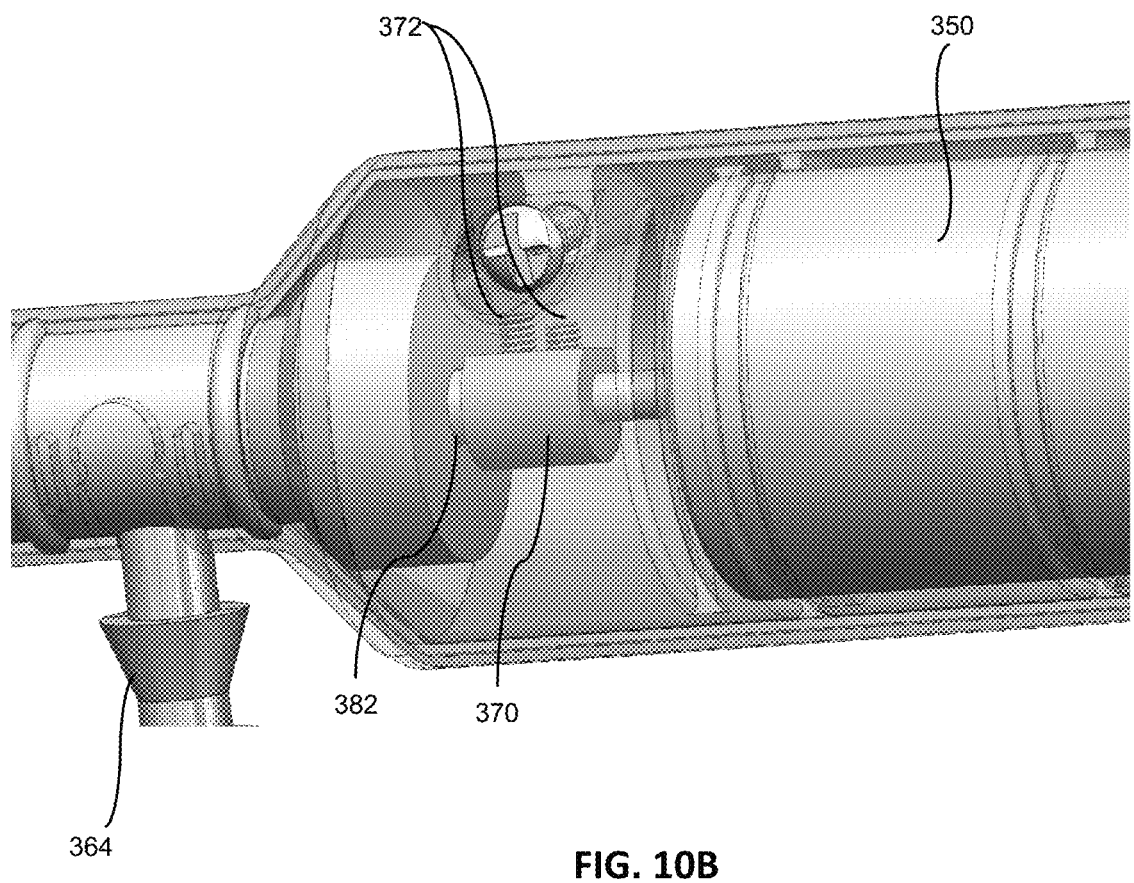
FIG. 10B is a partial transparent perspective view of one embodiment of a tissue resector according to the present invention.

The tissue resector 300 provides a rotary cutting action by rotating the inner cutting tube 382 relative to the static or non-rotating outer cutting tube 384. The inner cutting tube 382 is attached directly to the motor 350 by means of a coupler 370 and set screws 372 (FIG. 10A). The motor 350 providing a rotational output that rotates the inner cutting tube 382 relative to the outer cutting tube 384. The motor 350 is, for example, a direct current motor that is powered by the battery pack 340. For the sake of clarity, the resector 330 with motor 350 is configured to provide only a rotational tissue cutting function. For example, a rotational output in a range of 2,500 to 8,500 revolutions per minute, RPM.

In certain embodiments, the motor 350 is powered by a power source external to the handle 310 of the resector 300. For example, the handle 30 of the resector 300 may employ a feature such as a receptacle that receives an end of a power supply cable providing an external power source to drive the motor 350.

The outer cutting tube 384 is permanently and statically attached to the handle 310 and/or fluid chamber 360. For example, in one embodiment, the proximal end of the outer cutting tube 384 may employ a flare to create mechanical lock 387 (FIG. 9) to keep the outer cutter from separating from the TRD.

Figure 8:
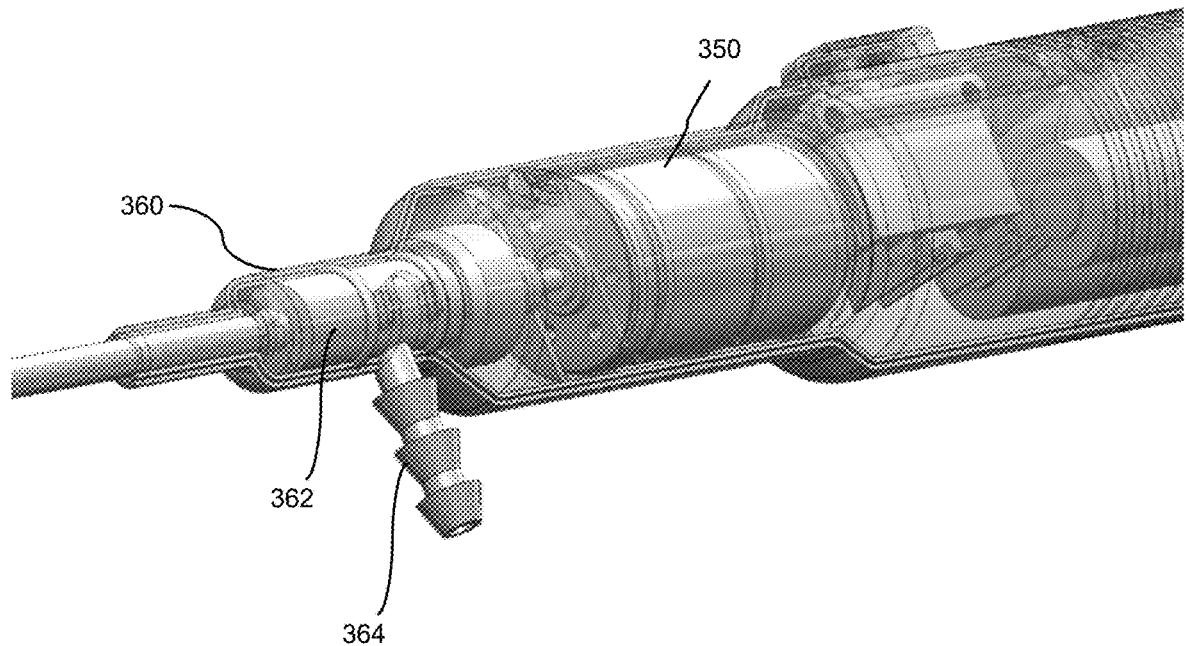
FIG. 8 is a partial transparent perspective view of one embodiment of a tissue resector according to the present invention.
Figure 9:
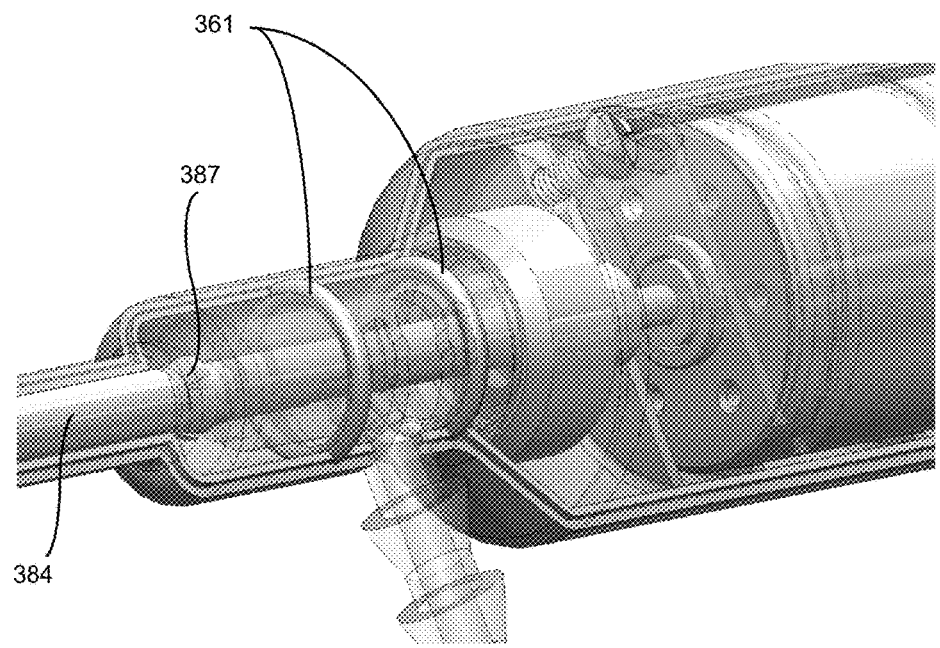
FIG. 9 is a partial transparent perspective view of one embodiment of a tissue resector according to the present invention.

The cutting tube assembly 380 employs an irrigation chamber 360 at the proximal portion (FIGS. 6A-6C). As shown in FIG. 8, the irrigation chamber 360 comprises a sealed cylinder 362 with a lateral port 364. The lateral port 364 connects to a vacuum line and is capable of swiveling within a given range of motion relative to the static handle 310. Cut pathological tissues and fluid entering the cutting windows 386a, 386b and/or distal holes 388a, 388b are pulled through an interior of the cutting tube assembly 380 by negative pressure. The pathological tissues and fluid flow into the sealed cylinder 362 inside the irrigation chamber 360 and out through the lateral port 364 connected to a vacuum line. The irrigation chamber 360 is housed in the narrow part of the handle 310 where a cut-out is created for the protruding lateral port 364 to provide a range of motion. The range of motion of the lateral port 364 may be in a range of 90 degrees to 180 degrees, e.g. −90 to 90 degrees, with respect to the user and of handle. The feature advantageously allows the outflow tubing (not shown) to be located down, left or right of the user. This is useful since the fluid management system or vacuum system can be either left or right of the user, thus allowing the outflow tubing position to be controlled according to user preference.

The irrigation chamber 360 is held in friction fit by sealing elements 361, allowing the port to stay at a desired position (FIG. 6C). A spacer 363 with a window is permanently attached or coupled where its window longitudinally aligns with a proximal window or aperture formed through a sidewall of the inner cutting tube 382. At the ends of the spacer 363 are sealing elements 365 to ensure the fluid and pathological tissues stay within the chamber or irrigation chamber 360 and keep the fluid and pathological tissues from entering into the handle 310.

The single-use tissue removal device (TRD) or tissue resector 300 is activated by simultaneously actuating the leaf spring trigger 312 and the momentary switch 320. The trigger 312 is integrated into each half-handle 310 and the momentary switch 320 is integrated into one side of the handle or housing so as to be actuated by a single finger, e.g. and index finger, of the user. The tissue resector 300 creates a rotary cutting action by spinning the inner cutting tube 382 relative to the outer cutting tube 384 when the leaf spring trigger 312 and momentary switch are concurrently actuated.

The hysteroscope and tissue resector are provided in various sizes based on the outer diameters of the lumens of the hysteroscope and tissue resector. The outer diameters of the lumens are chosen based on the ease of the instrument to enter into the uterus.

Herein, methods of using the inventive system employing the reusable multi-lumen hysteroscope 100, the single-use tissue removal device (TRD) or tissue resector 300; and, optionally, the modular outflow channel 200 is described. A light source is connected to the body 101 of the hysteroscope 100 at the light post 140. The distal ends of the Y-tubing 400 are connected to proximal portions of the irrigation lumens or channels 115 and 116 of the hysteroscope 100 and an opposite end of the Y-tubing 400 is connected to a fluid inflow source. Depending upon whether the resector 300 or the modular outflow channel 200 is to be initially employed within working channel 114 of the hysteroscope 100, a vacuum source is connected to either the coupler 364 of the resector 300 or to the outflow port 271 of the modular outflow channel 200.

The distal portion of the insertion section 102 of the hysteroscope 100 having the barrel 150 is inserted through the vagina and cervix and into the uterus of the patient. Fluid inflow, via lumens 115 and 116, and outflow, via working channel 114 of the resector 300 or lumen of the modular outflow channel 200, is manipulated in order to distend the uterus. After achieving an optimum fluid balance, the interior of the uterus and pathology is visually investigated.

If the modular outflow channel 200 is used to distend the uterus, after visual inspection of the uterus, channel 200 is removed from the working channel 114 of the hysteroscope 100 to allow insertion of the tissue resector 300 into the working channel 114. When the tissue resector 300 is fully inserted into the body 101 of the hysteroscope 100, a set length of the distal portion of the tissue resector 300 including the cutting windows 386a, 386b extends beyond the distal end of the hysteroscope 100 within the uterus. The tissue resector 300 is then activated by actuating the leaf spring trigger in the handle of the resector and concurrently actuating the momentary switch of the resector using a finger, e.g. a finger of the same hand of the user grasping the handle and leaf spring trigger, of the resector. The user then removes the pathology with the resector 300 while simultaneously visualizing the interior of the uterus and pathology through the lumen 112 of the optical system 110 of the hysteroscope 100. After removal of the pathology, the hysteroscope 100 and resector 300 are withdrawn from the patient.

While the above method has been described with relation to steps performed in a sequence, the above steps may be performed in alternative sequences and/or various steps may be performed simultaneously without departing from the spirit of the present invention.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A single-use uterine tissue resector comprising:
   a handle;
   an outer cutting tube having a proximal portion and a distal portion, wherein the proximal portion is statically attached to the handle, and wherein the distal portion includes a cutting window and a first distal hole;
   an inner cutting tube concentrically positioned and rotatable within a lumen of the outer cutting tube, wherein a distal end of the inner cutting tube includes a second distal hole;
   wherein the first distal hole and the second distal hole are configured to allow irrigation through the inner cutting tube when the cutting window is closed; and
   a motor positioned within the handle and coupled to a proximal end of the inner cutting tube, wherein upon activation of the motor, the motor rotates the inner cutting tube relative to the outer cutting tube; and
   a sealed cylinder positioned within the handle near the proximal portion of the outer cutting tube, the sealed cylinder comprising a port configured to be connected to a vacuum line so as to apply a negative pressure within the lumen.

2. The single-use uterine tissue resector of claim 1 wherein the port is movable with respect to the handle between a plurality of positions.

3. The single-use uterine tissue resector of claim 1 wherein the handle comprises a leaf spring trigger.

4. The single-use uterine tissue resector of claim 1 wherein the handle comprises a momentary switch.

5. The single-use uterine tissue resector of claim 1 wherein a distal end of the inner cutting tube and a distal end of the outer cutting tube form openings into a lumen of the inner cutting tube.

6. The single-use uterine tissue resector of claim 1 wherein a distal portion of the inner cutting tube and a distal portion of the outer cutting tube comprise apertures having cutting surfaces.

7. The single-use uterine tissue resector of claim 6 wherein the apertures of the inner and outer cutting tubes comprise a substantially same size, shape and longitudinal placement relative to one another.

8. The single-use uterine tissue resector of claim 1, wherein the port is comprised of a lateral port that protrudes out from the handle.

9. The single-use uterine tissue resector of claim 8, wherein a proximal portion of the inner cutting tube passes through the sealed cylinder, the proximal portion of the inner cutting tube having an aperture formed through a sidewall thereof.

10. The single-use uterine tissue resector of claim 8, wherein the handle comprises a cut-out through which the port of the sealed cylinder protrudes and is rotatable relative to the handle.

11. A medical system comprising:
    a single-use uterine tissue resector comprising:
      a handle;
      an outer cutting tube having a proximal portion statically attached to the handle and a distal portion comprising a cutting window and a first distal hole;
      an inner cutting tube concentrically positioned and rotatable within a lumen of the outer cutting tube, wherein a distal end of the inner cutting tube includes a second distal hole;
      wherein the first distal hole and the second distal hole are configured to allow irrigation through the inner cutting tube when the cutting window is closed; and
      a motor positioned within the handle and coupled to a proximal end of the inner cutting tube, wherein upon activation of the motor, the motor rotates the inner cutting tube relative to the outer cutting tube; and
      a sealed cylinder positioned within the handle adjacent to the proximal portion of the outer cutting tube, the sealed cylinder comprising a port, wherein the port is configured to be connected to a vacuum line so as to apply a negative pressure within the lumen, and wherein the port is movable with respect to the handle between a plurality of positions; and
    a hysteroscope comprising:
      a proximal body from which a multi-lumened distal outer tube extends;
      an optical lumen positioned through the proximal body and the distal outer tube having a fluid-sealed distal end configured to prevent a fluid entry into the optical lumen from a surgical site, and a proximal optical output extending upwardly from the proximal body, wherein the proximal optical output comprises an eyepiece;
      a light transmission lumen positioned through the proximal body and the distal outer tube having a fluid-sealed distal end configured to prevent the fluid entry into the light transmission lumen to the surgical site and a proximal light post configured for attachment to a light source;
      a working lumen positioned through the proximal body and the distal outer tube having an open distal end and an open proximal end and through which the resector is reversibly inserted;
      a seal disposed at a proximal end of the proximal body, the seal being configured to selectively seal the working lumen or to enable a friction fit for the single-use uterine tissue resector when the single-use tissue resector is inserted through the working lumen; and
      a first irrigation lumen positioned through the proximal body and the distal outer tube having an open distal end and a proximal valve.

12. The system of claim 11, further comprising a modular flow channel reversibly insertable through the working lumen of the hysteroscope.

13. The system of claim 11, wherein the optical lumen, the working lumen and the irrigation lumen are positioned within the light transmission lumen of the hysteroscope.

14. The system of claim 11, wherein the distal outer tube of the hysteroscope comprises an outer diameter of about 5.8 millimeters.

15. The system of claim 11, wherein the resector further comprises a battery positioned within the handle that is in electrical communication with the motor.

16. The system of claim 11, wherein the handle comprises a leaf spring trigger and a momentary switch.

* * * * *